US006955642B1

(12) United States Patent
Simon

(10) Patent No.: US 6,955,642 B1
(45) Date of Patent: Oct. 18, 2005

(54) PULSED ELECTROMAGNETIC FIELD STIMULATION METHOD AND APPARATUS WITH IMPROVED DOSING

(75) Inventor: Bruce J. Simon, Mountain Lakes, NJ (US)

(73) Assignee: EBI, LP, Parsippany, NJ (US)

( * ) Notice: Subject to any disclaimer, the term of this patent is extended or adjusted under 35 U.S.C. 154(b) by 0 days.

(21) Appl. No.: 10/304,721

(22) Filed: Nov. 26, 2002

(51) Int. Cl.$^7$ .................................................. A61N 1/00
(52) U.S. Cl. ........................................ 600/14; 607/50
(58) Field of Search .................. 600/9–15; 607/48–52, 607/61, 65, 72, 76

(56) References Cited

U.S. PATENT DOCUMENTS

| | | | |
|---|---|---|---|
| 3,893,462 | A | 7/1975 | Manning |
| 4,105,017 | A | 8/1978 | Ryaby et al. |
| 4,177,796 | A | 12/1979 | Franco-Vila |
| 4,266,533 | A | 5/1981 | Ryaby et al. |
| 4,315,503 | A | 2/1982 | Ryaby et al. |
| 4,683,873 | A | 8/1987 | Cadossi et al. |
| 4,758,429 | A | 7/1988 | Gordon |
| 4,998,532 | A | 3/1991 | Griffith |
| 5,014,699 | A | 5/1991 | Pollack et al. |
| 5,131,904 | A | 7/1992 | Markoll |
| 5,338,286 | A | 8/1994 | Abbott et al. |
| 5,366,435 | A | 11/1994 | Jacobson |
| 5,387,176 | A | 2/1995 | Markoll |
| 5,458,558 | A | 10/1995 | Liboff et al. |
| 5,518,496 | A | 5/1996 | McLeod et al. |
| 5,842,966 | A | 12/1998 | Markoll |
| 5,968,527 | A | 10/1999 | Litovitz |
| 6,099,459 | A | 8/2000 | Jacobson |
| 6,213,933 | B1 | 4/2001 | Lin |
| 6,261,221 | B1 | 7/2001 | Tepper et al. |
| 6,443,883 | B1 | 9/2002 | Ostrow et al. |

OTHER PUBLICATIONS

Goodman et al., "Exposure of Human Cells to Low-Frequency Electromagnetic Fields Results in Quantitative Changes in Transcripts," *Biochimica et Biophysica Acta*, 1009 (1989), pp. 216-220.

Rubin et al., "Prevention of Osteoporosis by Pulsed Electromagnetic Fields," *The Journal of Bone and Joint Surgery*, vol. 71A, No. 3, Mar. 1989, pp. 411-417.

Goodman et al., "Stimulation of RNA Synthesis in the Salivary Gland Cells of *Sciara Coprophila* by an Electromagnetic Signal Used for Treatment of Skeletal Problems in Horses," *Journal of Bioelectricity*, 6 (1), 1987, pp. 37-47.

Gray et al., "Suppression of LPS-Induced IL-1 Beta Production in Cultured Synoviocytes," 49th Annual Meeting of the Orthopaedic Research Society, New Orleans, Louisiana, Feb. 2-5, 2003, Poster #0737.

Ciombor et al., "Modification of Osteoarthritis by Pulsed Electromagnetic Field—A Morphological Study," *OsteoArthritis and Cartilage*, vol. 11, No. 6, 2003, pp. 455-462.

Aaron et al., "Upregulation of Basal TGFβ$_1$ Levels by EMF Coincident with Chondrogenesis—Implications for Skeletal Repair and Tissue Engineering," *Journal of Orthopaedic Research*, 20 (2002), pp. 233-240.

(Continued)

*Primary Examiner*—John P. Lacyk
(74) *Attorney, Agent, or Firm*—William F. Bahret

(57) ABSTRACT

A noninvasive method and apparatus for treating living tissue with pulsed electromagnetic fields (PEMFs) having selectively reduced high-frequency signal components, with improved bioresponse provided by magnetic field amplitudes less than approximately 40 $\mu$T, and most preferably in the range of 4–10 $\mu$T. Such amplitude levels for the disclosed PEMF signal are particularly effective with a treatment duration in the range of 0.25–2 hours/day.

22 Claims, 4 Drawing Sheets

OTHER PUBLICATIONS

Buechler et al., "Calculations of Electric Fields Induced in the Human Knee by a Coil Applicator," *Bioelectromagnetics*, 22 (2001), pp. 224-231.

Fredericks et al., "Effects of Pulsed Electromagnetic Fields on Bone Healing in a Rabbit Tibial Osteotomy Model," *Journal of Orthopaedic Trauma*, vol. 14, No. 2, 2000, pp. 93-100.

PULSED ELECTROMAGNETIC FIELD STIMULATION METHOD AND APPARATUS WITH IMPROVED DOSING

BACKGROUND OF THE INVENTION

This invention relates to the treatment of living tissue or cells with electromagnetic fields, and particularly to such treatment employing pulsed electromagnetic fields (PEMFs).

It is well known that time-varying low-energy electric or magnetic fields produce a range of responses in biological systems. In particular, low-energy fields which are essentially athermal are increasingly used for therapeutic purposes as in the healing of fractures and ulcers, assisting bone graft incorporation, etc. The precise mechanisms of action of these low-energy fields are not well understood, but there is evidence that the responses relate to the direct effects of both magnetic and electric fields. Magnetic fields may also act through the induction of electric fields in tissue or cells, and time-varying electric fields may be produced by induction, capacitative coupling or by use of implanted electrodes.

A variety of time-varying electromagnetic waveforms have been studied, patented and used in practice. The widest present application is of electric field inputs to tissue induced by an asymmetrically rising and falling magnetic field as described, e.g., in the following patents:

| U.S. Pat. No. | Inventor | Issue Date |
|---|---|---|
| 3,893,462 | Manning | Jul. 8, 1975 |
| 4,105,017 | Ryaby et al. | Aug. 8, 1978 |
| 4,266,533 | Ryaby et al. | May 12, 1981 |
| 4,315,503 | Ryaby et al. | Feb. 16, 1982 |
| 4,683,873 | Cadossi et al | Aug. 4, 1987 |

The waveforms of these induced electric inputs are generally described by a quasi-rectangular or trapezoidal-shaped excursion of the electric (E) field followed either by a narrower excursion of higher amplitude in the reverse direction in the case of pulse trains or "bursts," or by a broad low-amplitude excursion in the case of some repetitive single pulses. It is also known from, e.g., U.S. Pat. No. 4,998,532 to Griffith and U.S. Pat. No. 5,014,699 to Pollack, that more symmetrical pulsed fields produced, for example, by switching abruptly between positive and negative electric fields (achieved, for example, by switching the polarity of the current input to a low inductance coil to give a series of rising and falling magnetic fields in the target tissue or cell system) are also bioactive.

A characteristic of the waveforms in these cases is that abrupt changes occur in the magnitudes or directions of the electric or magnetic fields. For example, in commercial application of the waveforms described by Ryaby et al., the induced electric field rises from zero to its quasi-rectangular "positive" ongoing form or reverses sign to a higher-amplitude narrow "negative" excursion in a time interval of about one microsecond or less, as compared to pulse widths typically on the order of tens to thousands of microseconds. Correspondingly, the time derivative of the magnetic field changes sign over an interval of about one microsecond, whereas the intervals in which the sign is unchanged are typically ten or more times as long. In the work of Griffith and Pollack, the preferred pulse widths are on the order of ten microseconds, these pulses being repeated in bursts on the order of milliseconds. The reversal time for these pulses is typically one microsecond or less. Trains of pulses as in the above-referenced Ryaby et al. patents, all of which are hereby incorporated by reference, typically last for milliseconds and the pulses or pulse trains are repeated at intervals on the order of tens to thousands of milliseconds. Still, in commercially available equipment generating such pulse trains, the rise and fall times for individual pulses are abrupt, i.e., about one microsecond or less.

In some cases, the abrupt changes in the time derivative of the electric field may be associated with overshooting, which may include a damped oscillation or ringing on the order of 1 MHz, i.e., within the range of about 0.5 to 5 MHz. The frequency content of asymmetric pulse waveforms of the Ryaby et al. type, as derived by discrete Fourier Transforms, can range to 10 MHz, as described by Goodman et al. in a paper entitled "Exposure of Human Cells to Low-Frequency Electromagnetic Fields Results in Quantitative Changes in Transcripts," in Biochimica et Biophysica Acta, 1009 (1989) 216–220.

The bioresponse of PEMF signals with rapidly changing pulses can be improved by signal shaping to reduce the high-frequency components of the signals, as described in U.S. Pat. No. 5,338,286 to Abbott et al., which patent is hereby incorporated by reference. In terms of the time domain, significant improvement in the bioefficacy of low-energy pulsed electromagnetic signals configured with waveforms ordinarily characterized by abrupt changes in magnitude or sign of the electric or magnetic field is achievable by reducing or eliminating one or more of the previously characteristic abrupt changes and providing smoother transitions to relatively flat segments or portions of the signal or waveform. "Abrupt" in this context is intended to connote time intervals of approximately 1 microsecond or less.

SUMMARY OF THE INVENTION

The present invention provides a method and apparatus for obtaining further improvements in bioresponse using a PEMF signal such as that disclosed in the above-referenced Abbott et al. patent. The present invention is based on the unexpected discovery of certain relatively low signal amplitude and/or dosage levels at which such a PEMF signal is more effective than at other amplitude and/or dosage levels. The PEMF signal described herein is useful for electrical stimulation of bone growth, not only in cases of non-unions and delayed unions but also in cases of fresh fractures, and wound healing in general, and is also useful in the treatment of osteoarthritis, the leading cause of disability in Americans 65 years old and older.

It is a general object of the present invention to provide improved bioresponse of PEMF signals used for treatment of living tissue and cells, and in particular bone and cartilage.

A further object of the invention is to make known PEMF signals more effective by providing such signals at relatively low amplitude and/or dosage levels.

These and other objects and advantages of the present invention will be more apparent upon reading the following detailed description in conjunction with the accompanying drawings.

DESCRIPTION OF PREFERRED EMBODIMENTS

Figure 1:
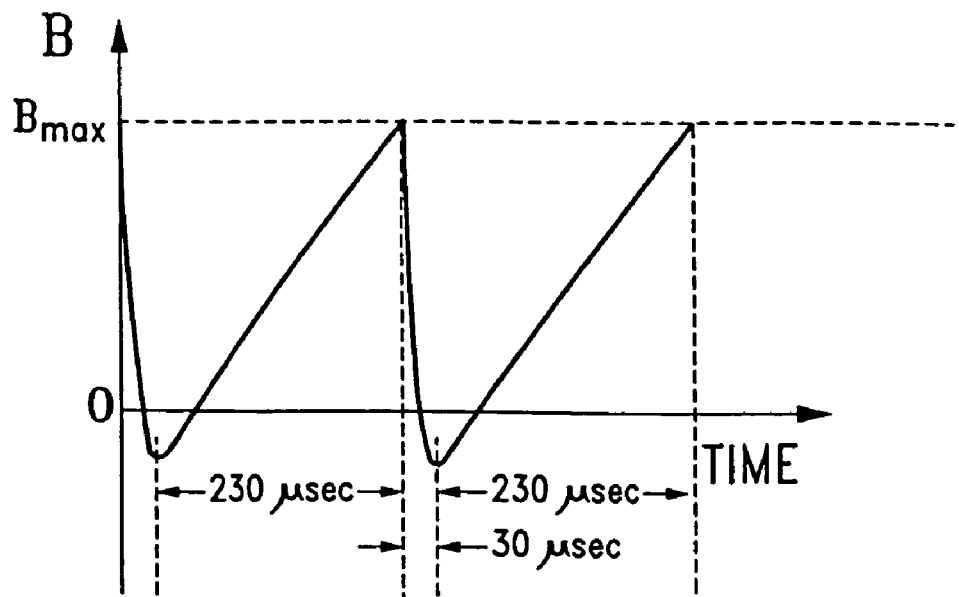
FIG. 1 illustrates a magnetic field waveform according to a preferred embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates, for example, in the use of signal forms as herein described delivered by capacitative or implanted electrodes.

Figure 2:
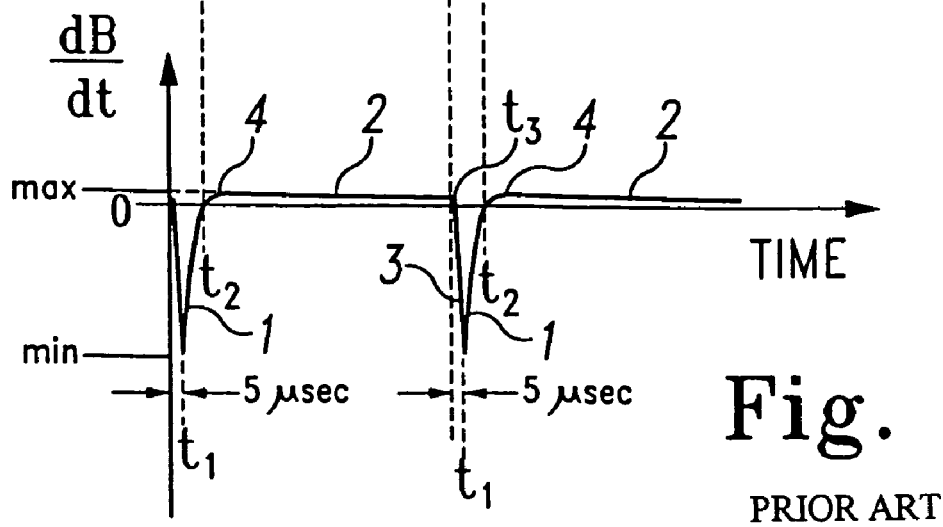
FIG. 2 illustrates the time derivative of the magnetic field waveform of FIG. 1, as well as the electric field induced by that magnetic field.

FIGS. 1 and 2 illustrate the magnetic field waveform (magnetic flux density B) and the time derivative thereof (dB/dt), respectively, for a stimulatory waveform for use in bone and tissue healing according to a preferred embodiment of the present invention. The shape of the waveform of FIG. 2 also corresponds to the electric field, as would be measured with a suitable inductive pickup, which is produced by induction from the magnetic field of FIG. 1 passing through the tissue or cells. Those skilled in the art will appreciate that the induced electric field is directly proportional to the rate of change of flux density with respect to time (dB/dt). FIG. 2 also corresponds in shape to the waveform of the voltage across the treatment coil driven by a preferred embodiment of a signal generator according to the present invention, to be described with reference to FIGS. 3 and 4. The principles of the invention will apply equally to single repetitive pulses or to pulse trains as described in the above-referenced Ryaby et al. patents, and it is to be understood that FIGS. 1 and 2 represent a portion of a pulse burst sufficient to show the details of an individual pulse as well as the transition between pulses in the pulse burst. As shown in FIG. 1, one example of a suitable PEMF signal according to the present invention has a pulse period of approximately 260 microseconds, with a positive-going pulse portion of approximately 230 microseconds (reflected in FIG. 2 as the positive portion of each dB/dt pulse). The pulses are preferably delivered in pulse bursts approximately 30 milliseconds in duration, at a burst repetition rate of approximately 1.5 Hz.

It has been found that the bioresponse of PEMF signals is sharply improved when the rise and fall times in the electric field are lengthened, and, in particular, when the amplitude changes are made less abrupt by rounding the profile of the pulses. An example of such rounding is shown in FIG. 2, particularly in the approximately exponential shape of leading edge 1 of an individual pulse having a relatively flat top segment 2 and a trailing edge 3, the pulse having a smooth transition 4 from leading edge 1 to the relatively flat top segment 2 as shown in the drawing. The rounding will usually be associated with some increase in the rise and fall times, as is also shown in FIG. 2, in which the time interval from time $t_1$ to time $t_2$, when the E field signal crosses zero, is 25 microseconds, and the time to reach the signal maximum from $t_1$ is about 30 microseconds, with the signal generator and treatment coil to be described with reference to FIG. 3. The corresponding fall time, i.e., the interval from $t_3$ to $t_1$, is 5 microseconds. Most preferably, the leading edge is continuously smooth for the entire interval from $t_1$ to the signal maximum, and the trailing edge is continuously smooth for the entire interval from $t_3$ to $t_1$. That is, there is no discontinuity in the signal or abrupt portion associated with either edge.

The circuitry to be described produces the desired rounding while maintaining the amplitude of the signal over most of its relatively flat top segment 2, whereas the negative amplitudes of pulse trains of the Ryaby et al. type after smoothing will usually not be as high. In the case of certain single repetitive pulses as described in the Ryaby et al. patents, in which relatively shallow, long negative excursions are effective, the positive and negative amplitudes of the electric field are readily maintained over most of the relevant excursion periods, and the changes in the overall waveform constitute primarily an extension of the rise and fall times and a rounding of the terminal portion of the rising and trailing edges. It is to be understood that "positive" and "negative" as well as terms such as "rise" and "fall" time are intended as relative terms for reference purposes in the description of pulse portions of opposite polarity with respect to a reference potential level. It is contemplated that similar rounding and extension of the edges of sharp square-wave pulses such as taught by Griffith and Pollack et al. will similarly result in improved bioresponse. Rectangular pulses, quasi-rectangular pulses, and trapezoidal pulses, among others, are all considered to have a relatively flat top segment in the context of this invention, and improved bioresponse would be anticipated upon appropriate rounding of the profiles of such pulses in accordance with the teachings of this invention.

As disclosed in further detail in U.S. Pat. No. 5,338,286, frequency components above 50 kHz and particularly above 200 kHz are selectively reduced by the circuitry according to the preferred embodiments of the present invention. The frequency spectra of other signals presently used also include a large number of equivalent spectral lines including higher frequency components in the range of 50 kHz to 5 MHz corresponding to the abrupt edges, ramps, overshoot and ringing in those signals, and it is believed that the effectiveness of all such signals can be improved by selective reduction of component frequencies as described above.

Figure 3:
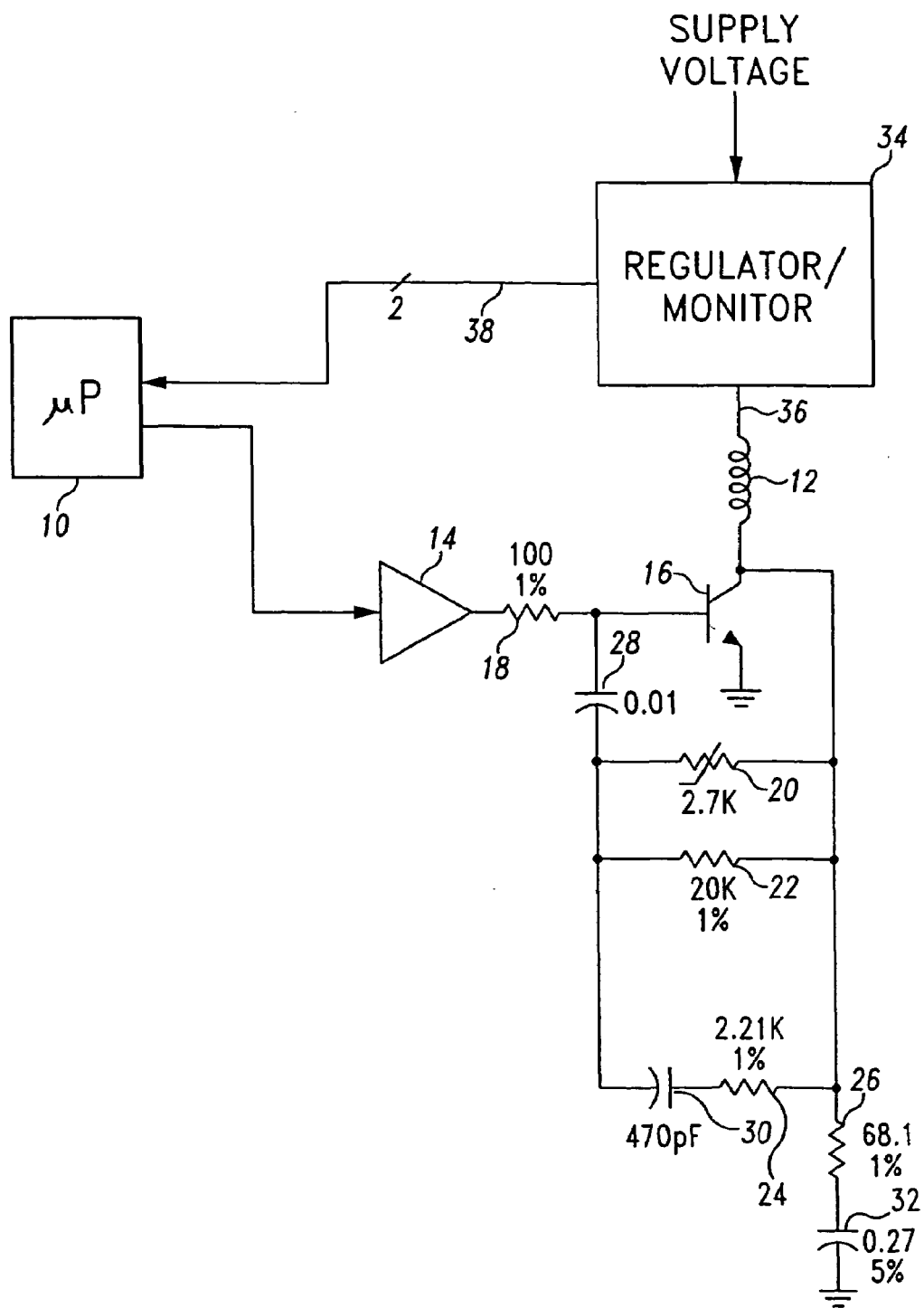
FIG. 3 is an electrical schematic of a pulse generator according to one embodiment of the present invention.

Referring now to FIG. 3, a pulse generator capable of producing such improved bioresponse and, in particular, capable of producing the signals shown in FIGS. 1 and 2, will be described. The timing and pulse width of the individual pulses in each pulse train as well as the burst width and burst repetition rate are controlled by a microprocessor 10 which is appropriately programmed for such purposes in a manner well known to those skilled in the art. Further description of control units for control of such parameters, as well as circuitry designed to accommodate changes in pulse width and repetition rate, for example, in the course of a given body treatment according to a predetermined pattern or program of variation, may be found in the above-referenced U.S. Pat. No. 4,315,503 to Ryaby et al., and such descriptions in particular are hereby incorporated by reference along with the entirety of said patent. Microprocessor 10 generates a drive signal for the treatment coil 12, the drive signal as supplied by the microprocessor taking the form of bursts of individual square-wave pulses. In the drive signal corresponding to the signals of FIGS. 1 and 2, each has a pulse width of approximately 230 microseconds, followed by a 30-microsecond interval prior to the next pulse, and the pulses are supplied in 30-millisecond bursts at a repetition rate of 1.5 Hz.

The microprocessor supplies the drive signal through driver amplifier 14 to a signal shaping circuit built around a transistor 16 and including resistors 18, 20, 22, 24 and 26 and capacitors 28, 30 and 32 interconnected as shown in the drawing. Resistors 18, 20 and 22 and capacitor 28 form a negative voltage shunt feedback loop to control the signal negative amplitude. Resistor 20 is a positive temperature coefficient (PTC) device which compensates for $V_{BE}$ temperature variations in transistor 16. Capacitor 30 and resistor 24 control the trailing edge slope of the signal, while capacitor 32 and resistor 26 control the leading edge slope. A pulse generator with the component values shown in FIG. 3, and with a treatment coil with an inductance of about 500 millihenries, produces a magnetic field as in FIG. 1 with a peak magnetic flux density ($B_{max}$) of 2 Gauss, or 200 $\mu T$ (microTesla). One such treatment coil is the FLX-2 coil, and, for different applications, one may employ other coils in the FLX family line, all commercially available from Electro-Biology, Inc. Other values of treatment coil inductance are disclosed in the above-referenced Ryaby et al. patents incorporated herein by reference.

A regulated voltage level of approximately 1 volt DC is established by a regulator/monitor circuit 34, one output of which is connected to treatment coil 12 via line 36. Regulator/monitor 34 also has a pair of output lines 38 to the microprocessor for monitoring purposes as described in U.S. Pat. No. 5,338,286.

In addition to the methods already described for increasing the required time constant to round or smooth the abrupt edges, the inductance of the treatment coil may be increased or, in the case of a capacitively coupled electric signal, series resistance can be added to increase the time constant to, e.g., 5 milliseconds. Alternatively, resonant circuits using series/parallel arrangements of resistors, inductors and capacitors, including the values for the primary delivery element for the desired localized field, i.e., the coil or capacitor placed at the treatment site or used to stimulate tissue cultures, etc., may be employed.

Figure 4:
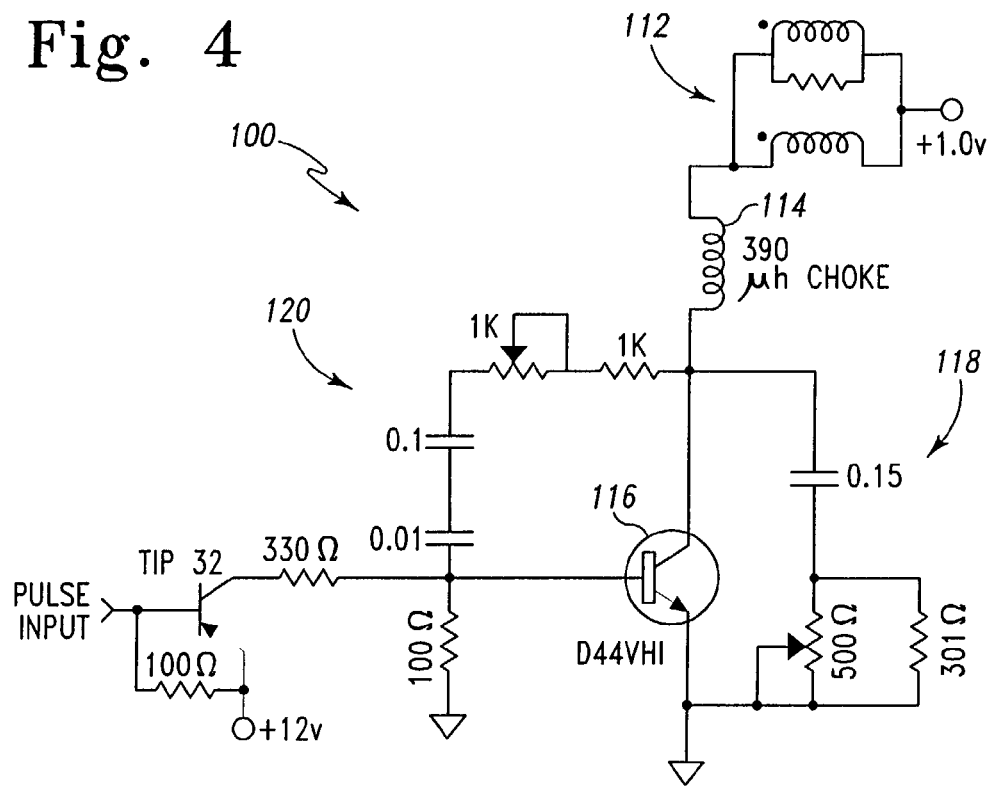
FIG. 4 is an electrical schematic of an alternative pulse generator according to the present invention.

FIG. 4 shows an alternative pulse generator 100 suitable for producing signals of the type shown in FIGS. 1 and 2. The circuit includes a treatment head 112 connected through a choke 114 to a transistor 116 and a signal shaping network which includes first and second RC networks 118 and 120 for control of the rise time and fall time, respectively, of the waveform of the voltage across the treatment coil and thus of the dB/dt waveform (FIG. 2). The treatment head in one embodiment has two coils spaced apart from each other, e.g., by approximately 15 cm, each coil approximately 30–35 cm square and formed of 10 turns of 18G wire, for example, with a total inductance of approximately 70 mH and total resistance of approximately 0.2 ohms. The treatment head is connected on one end to a regulated 1 VDC supply as described above. With such a treatment head and with the component values shown in FIG. 4, the pulse generator produces a PEMF with a peak amplitude of approximately 100 mG, or 10 $\mu T$, and a maximum dB/dt of approximately 0.06 T/sec and minimum dB/dt of approximately −0.9 T/sec.

Surprisingly, it has been found that a PEMF signal such as shown in FIG. 1 is more effective at such a lower amplitude than at the 2 G (200 $\mu T$) amplitude described above, for enhancement of growth of both bone and cartilage. The peak amplitude of the magnetic field is preferably in the range of 0.8–40 $\mu T$, and a more preferred range is 2–20 $\mu T$. The range of 4–10 $\mu T$ is presently most preferred. The signal is effective with treatment duration in the range of 0.25–8 hours/day and particularly effective with the duration in the range of 0.25–2 hours/day.

EXAMPLE 1

Figure 5:
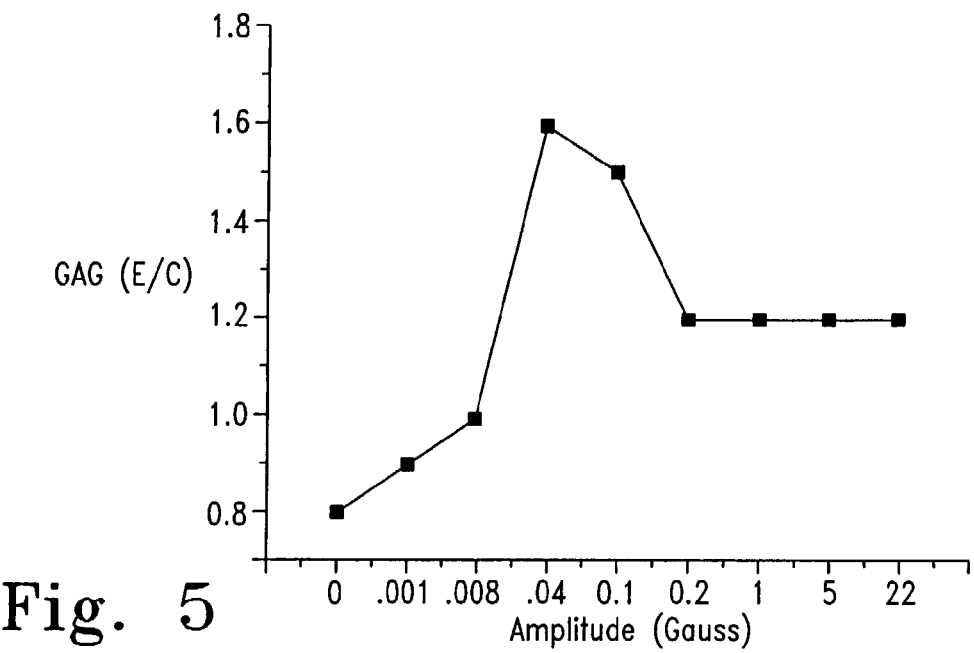
FIG. 5 is a graph of results from an in vivo dose response study in a rat ossicle model.

PEMF enhancement of chondrogenesis, the growth of cartilage, has been demonstrated in several animal studies. For example, demineralized bone matrix (DBM) was implanted subcutaneously in the rat ossicle model. Animals were exposed to PEMFs of different amplitudes and durations using a pulse generator of the type described above. On day 8 after implantation, levels of glycosaminoglycan (GAG), a marker of chondrogenesis, were determined. FIG. 5 shows normalized (GAG) levels (experimental values over control values (E/C)), as a function of signal amplitude for 1 hr/day stimulation. There was a 50–60% enhancement of chondrogenesis occurring with a peak level of magnetic flux density in the range of 0.04–0.1 gauss (4–10 $\mu T$) At 0.1 gauss stimulation, a duration dose response study showed enhancement of chondrogenesis with durations of 1 to 4 hrs/day with peak stimulation at 1 hr/day.

EXAMPLE 2

Figure 6:
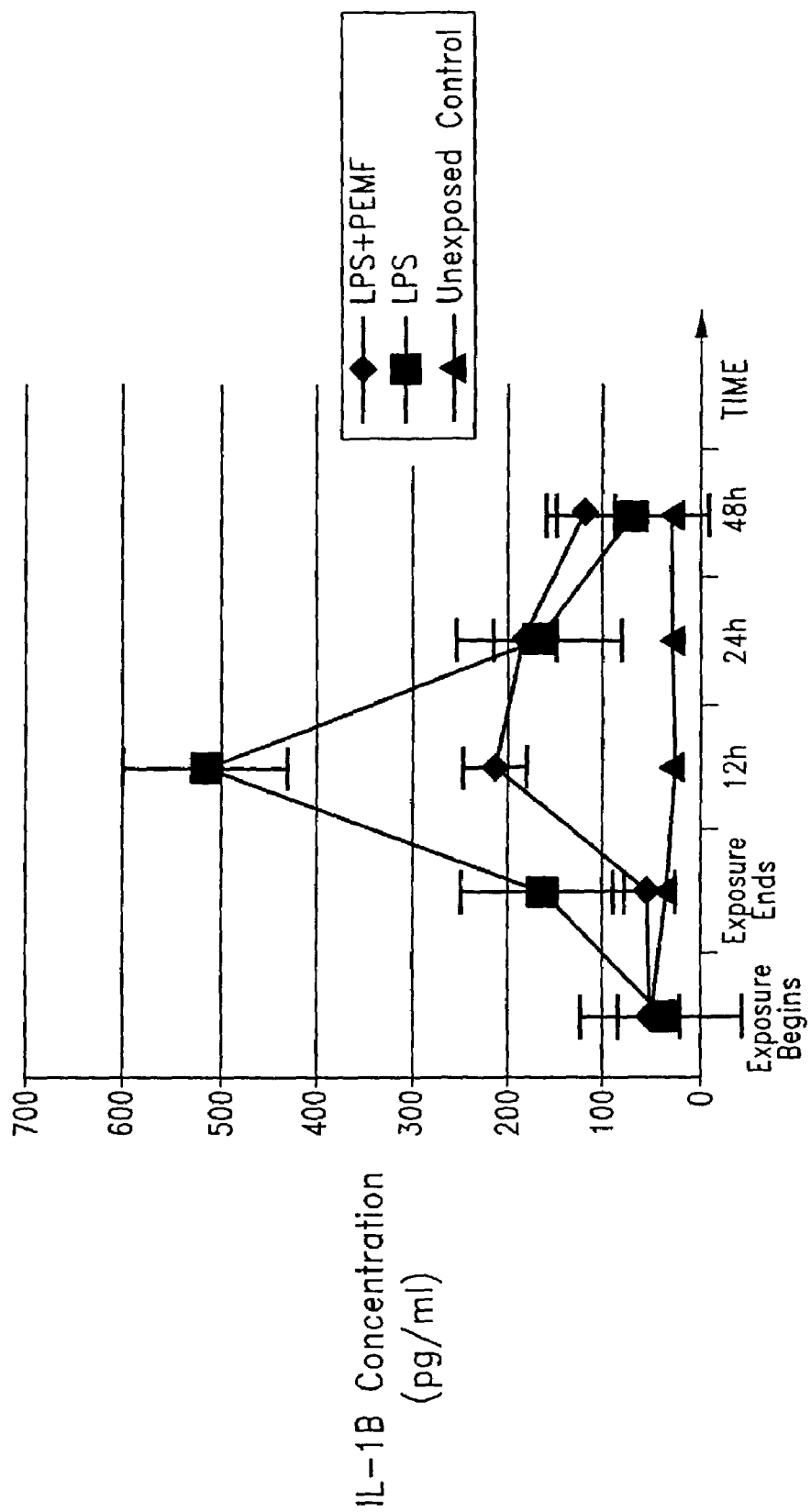
FIG. 6 is a graph of results from an in vitro IL-1β study in cultured porcine synoviocytes.

Interleukin-1β (IL-1β) is an important mediator of osteoarthritis (OA) because it induces nitric oxide production and its attendant destructive effects, and also produces chondrocyte-mediated matrix degradation. Transforming growth factor-β (TGFβ) limits the catabolic activity of IL-1β in cartilage and has been shown to stimulate cartilage repair. Experiments in the Hartley guinea pig (which spontaneously develops OA) using this PEMF signal at 1 gauss, demonstrated inhibition of cartilage degradation, a decrease in catabolic enzymes and IL-1β and an increase in TGFβ. A second experiment using the preferred 0.1 gauss amplitude PEMF signal again showed an inhibition of IL-1β production (FIG. 6). In this experiment, synoviocyte cultures from porcine knees were stimulated to release IL-1β by exposure to lipopolysaccharide (LPS). LPS drastically increased levels of IL-1β during the 12-hour exposure duration. PEMF stimulation during this time completely abolished the LPS induced rise in IL-1β. During the following 12 hrs when the synoviocytes were no longer exposed to either the LPS or PEMF, IL-1β levels continued to rise in the control cultures but were significantly reduced in the cultures previously treated with PEMF. Since in OA, cells of the synoviium produce IL-1β, which is responsible for cartilage matrix degradation, these data suggest that this PEMF signal may be of therapeutic value in retarding or reversing the progression of this disease.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A noninvasive apparatus for treating living tissue by means of a pulsed electromagnetic field, comprising:
    means for generating a drive signal including a series of pulses having high-frequency components associated with abrupt changes in value; and means responsive to said drive signal for generating a pulsed electromagnetic field with a peak-to-peak amplitude less than approximately 40 µT effective to produce a therapeutic bioresponse when coupled to an afflicted body part to be treated, said pulsed electromagnetic field generating means including signal shaping means for selectively reducing signal components of said drive signal at frequencies above 50 kHz.

2. The apparatus of claim 1, wherein said magnetic field amplitude is in the range of 2–20 µT.

3. The apparatus of claim 2, wherein said magnetic field amplitude is in the range of 4–10 µT.

4. A noninvasive apparatus for treating living tissue by means of a pulsed electromagnetic field, comprising:
   a treatment coil;
   means for noninvasively mounting said treatment coil in proximity to an afflicted body part to be treated; and
   electronic generator means coupled to said treatment coil for generating a pulse train in said treatment coil effective to produce a pulsed electromagnetic field having a peak-to-peak amplitude less than approximately 40 µT, said pulse train including pulses each having a leading edge, a trailing edge and a relatively flat peak therebetween, said pulses having a smooth transition on at least one of said edges immediately adjacent said relatively flat peak.

5. The apparatus of claim 4, wherein said magnetic field amplitude is in the range of 2–20 µT.

6. The apparatus of claim 5, wherein said magnetic field amplitude is in the range of 4–10 µT.

7. A method of treating osteoarthritis, comprising:
   positioning a treatment coil in proximity to an arthritic joint; and
   applying a pulsed electromagnetic field to said arthritic joint via said treatment coil, said pulsed electromagnetic field characterized by asymmetrical magnetic field pulses having a peak-to-peak amplitude less than approximately 40 µT.

8. The method of claim 7, wherein said magnetic field amplitude is in the range of 2–20 µT.

9. The method of claim 8, wherein said magnetic field amplitude is in the range of 4–10 µT.

10. The method of claim 9, wherein said pulsed electromagnetic field is applied to said arthritic joint for a treatment duration in the range of 0.25–8 hours/day.

11. The method of claim 10, wherein said pulsed electromagnetic field is applied to said arthritic joint for a treatment duration in the range of 0.25–2 hours/day.

12. The method of claim 7, wherein said pulsed electromagnetic field is applied to said arthritic joint for a treatment duration in the range of 0.25–2 hours/day.

13. A noninvasive method of treating damaged living tissue by means of a pulsed electromagnetic field, comprising:
   generating a drive signal including a series of pulses having high-frequency components associated with abrupt changes in value; and
   generating, in response to said drive signal, a pulsed electromagnetic field with a peak-to-peak amplitude less than approximately 40 µT effective to produce a therapeutic bioresponse when coupled to an afflicted body part having damaged tissue to be treated;
   wherein said pulsed electromagnetic field is generated with signal shaping means for selectively reducing signal components of said drive signal at frequencies above 50 kHz, and
   wherein said pulsed electromagnetic field is applied to said afflicted body part for a treatment duration in the range of 0.25–8 hours/day.

14. The method of claim 13, wherein said pulsed electromagnetic field is applied to said afflicted body part for a treatment duration in the range of 0.25–2 hours/day.

15. The method of claim 14, wherein said magnetic field amplitude is in the range of 2–20 µT.

16. The method of claim 15, wherein said magnetic field amplitude is in the range of 4–10 µT.

17. The method of claim 13, wherein said magnetic field amplitude is in the range of 4–10 µT.

18. A noninvasive method of treating damaged living tissue by means of a pulsed electromagnetic field, comprising:
   noninvasively mounting a treatment coil in proximity to an afflicted body part having damaged tissue to be treated; and
   generating a pulse train in said treatment coil effective to produce a pulsed electromagnetic field having a peak-to-peak amplitude less than approximately 40 µT, said pulse train including pulses each having a leading edge, a trailing edge and a relatively flat peak therebetween, said pulses having a smooth transition on at least one of said edges immediately adjacent said relatively flat peak;
   wherein said pulsed electromagnetic field is applied to said afflicted body part for a treatment duration in the range of 0.25–8 hours/day.

19. The method of claim 18, wherein said pulsed electromagnetic field is applied to said afflicted body part for a treatment duration in the range of 0.25–2 hours/day.

20. The method of claim 19, wherein said magnetic field amplitude is in the range of 2–20 µT.

21. The method of claim 20, wherein said magnetic field amplitude is in the range of 4–10 µT.

22. The method of claim 18, wherein said magnetic field amplitude is in the range of 4–10 µT.

* * * * *